(12) United States Patent
Chen

(10) Patent No.: US 11,459,052 B2
(45) Date of Patent: Oct. 4, 2022

(54) CONTROL METHOD FOR USE WITH LONGITUDINAL MOTION-SENSING TWO-WHEELED VEHICLES AND CONTROL SYSTEM

(71) Applicant: HANGZHOU CHIC INTELLIGENT TECHNOLOGY CO., LTD, Zhejiang (CN)

(72) Inventor: Hui Chen, Zhejiang (CN)

(73) Assignee: HANGZHOU CHIC INTELLIGENT TECHNOLOGY CO., LTD, Zhejiang (CN)

( * ) Notice: Subject to any disclaimer, the term of this patent is extended or adjusted under 35 U.S.C. 154(b) by 728 days.

(21) Appl. No.: 16/475,131

(22) PCT Filed: Mar. 3, 2017

(86) PCT No.: PCT/CN2017/075512
§ 371 (c)(1),
(2) Date: Jul. 1, 2019

(87) PCT Pub. No.: WO2018/120411
PCT Pub. Date: Jul. 5, 2018

(65) Prior Publication Data
US 2019/0328283 A1    Oct. 31, 2019

(30) Foreign Application Priority Data
Dec. 29, 2016 (CN) .......................... 201611249777.7

(51) Int. Cl.
*A61B 5/11* (2006.01)
*B62K 11/00* (2006.01)
(Continued)

(52) U.S. Cl.
CPC .............. *B62K 11/007* (2016.11); *A61B 5/11* (2013.01); *B60K 26/02* (2013.01); *B60L 15/20* (2013.01);
(Continued)

(58) Field of Classification Search
CPC ......................... B60K 11/007; B62K 2204/00
See application file for complete search history.

(56) References Cited

U.S. PATENT DOCUMENTS 8,738,278 B2 *   5/2014   Chen ................... B62K 11/007
                                                          701/99
2014/0131126 A1 *  5/2014  Martinelli ........... B62K 11/007
                                                          180/218
(Continued)

FOREIGN PATENT DOCUMENTS

CN          203844935          9/2014
CN          204775712          11/2015
(Continued)

OTHER PUBLICATIONS

"International Search Report (Form PCT/ISA/210) of PCT/CN2017/075512," dated Sep. 20, 2017, with English translation thereof, pp. 1-4.

*Primary Examiner* — Brian L Swenson
(74) *Attorney, Agent, or Firm* — JCIPRNET

(57) ABSTRACT

A control method for use with longitudinal motion-sensing two-wheeled vehicles is provided. The control method includes: collecting posture data of a human body leaning forward and backward and controlling an output of a circuit drive module to thereby control a rotational output of a motor; a motor rotor of the motor outputting a movement vector and an acceleration to control a rotation of wheels under the control of the output of the circuit drive module, a motor stator receiving a reaction force during a rotating and outputting process of the motor rotor, and the reaction (Continued)

force being transmitted to a motion-sensing platform through a mechanical structure by the motor stator, and the motion-sensing platform transferring and feeding back the reaction force to a user standing on the motion-sensing platform, thereby adjusting posture data of the motion-sensing platform again by means of a human body posture to achieve a motion-sensing balance control.

4 Claims, 1 Drawing Sheet

(51) Int. Cl.
*B60K 26/02* (2006.01)
*B60L 15/20* (2006.01)
*B62J 45/416* (2020.01)
*B62J 45/42* (2020.01)

(52) U.S. Cl.
CPC ............. *B62J 45/416* (2020.02); *B62J 45/42* (2020.02); *B62K 2204/00* (2013.01)

(56) References Cited

U.S. PATENT DOCUMENTS

| | | | | |
|---|---|---|---|---|
| 2014/0326525 | A1* | 11/2014 | Doerksen | A63C 17/26 |
| | | | | 180/181 |
| 2016/0291599 | A1* | 10/2016 | Doerksen | A63C 17/12 |
| 2018/0072367 | A1* | 3/2018 | Li | A63C 17/014 |
| 2018/0111039 | A1* | 4/2018 | Wood | A63C 17/12 |
| 2019/0291806 | A1* | 9/2019 | Martinelli | B62J 43/28 |

FOREIGN PATENT DOCUMENTS

| | | |
|---|---|---|
| CN | 105151193 | 12/2015 |
| CN | 205022758 | 2/2016 |
| WO | 2016095209 | 6/2016 |

* cited by examiner

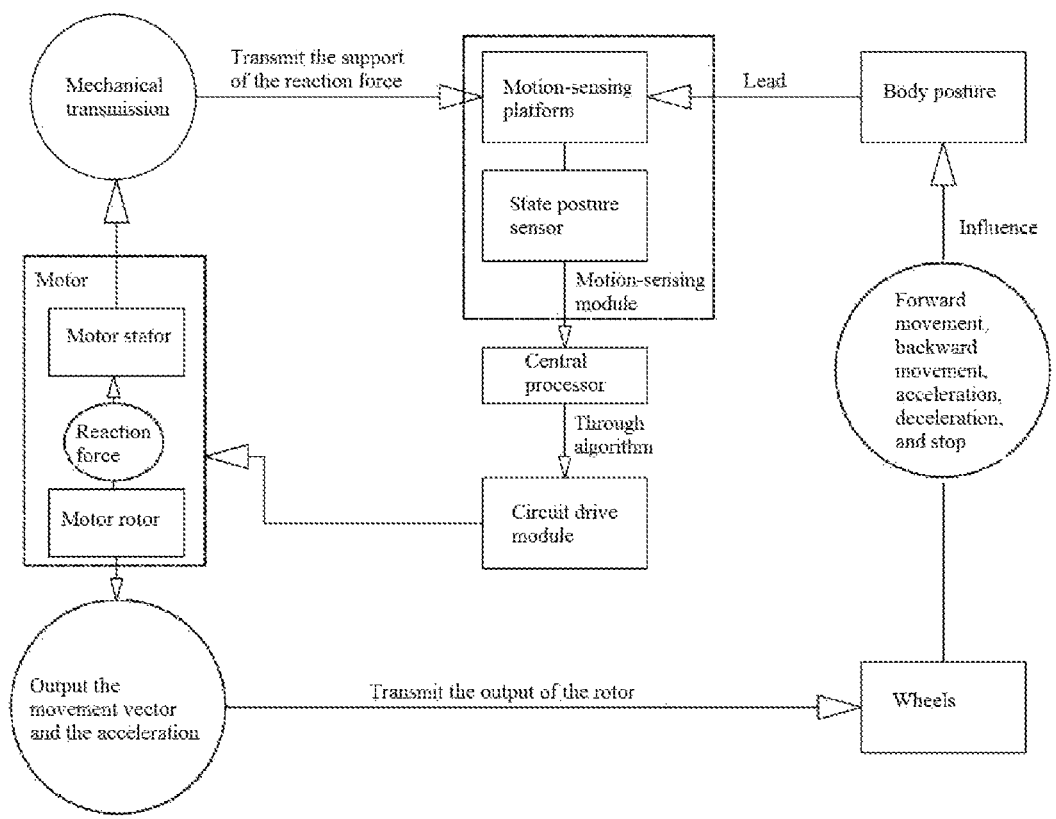

CONTROL METHOD FOR USE WITH LONGITUDINAL MOTION-SENSING TWO-WHEELED VEHICLES AND CONTROL SYSTEM

CROSS-REFERENCE TO RELATED APPLICATION

This application is a 371 of international application of PCT application serial no. PCT/CN2017/075512, filed on Mar. 3, 2017, which claims the priority benefit of China application no. 201611249777.7, filed on Dec. 29, 2016. The entirety of each of the above mentioned patent applications is hereby incorporated by reference herein and made a part of this specification.

BACKGROUND

Technical Field

The disclosure relates to a control method for a longitudinal motion-sensing two-wheeled vehicle and to a control system.

Description of Related Art

With the development of electric vehicles and the improvement of people's living standards, electric vehicles have become the main daily means of transportation for people. In particular, two-wheeled vehicles are more useful in sightseeing or patrol. For example, motion-sensing electric balance vehicles detect the posture change of the vehicle body based on the gyroscope and the acceleration sensor inside the vehicle body and are driven by the motor to achieve the vehicle body motion balance. In recent years, they have been widely used as means of transportation for leisure and patrol in eco-tourism scenic areas, large parks, airports and high-class communities. However, the movement speed of conventional motion-sensing electric balance vehicles on the market is generally recommended to be less than 15 yards per hour. When the speed is too high, it is likely to cause overcurrent and cause the motherboard to be burned out. In addition, when a conventional motion-sensing electric balance vehicle loses directional control and is about to fall, since the wheels are disposed on the left and right sides of the human body and the front handle is disposed in front of the human body, it causes the human body to be unable to come down from the balance vehicle in time and in the end causes the human body to fall down with the balance vehicle together, which is likely to cause a safety accident. Therefore, the applicant developed a longitudinal motion-sensing two-wheeled vehicle having a simple structure and allowing for a safe and reliable use.

SUMMARY

An object of the disclosure is to provide a control method for a longitudinal motion-sensing two-wheeled vehicle, so that the two-wheeled vehicle automatically achieves a motion-sensing balance.

Another object of the disclosure is to provide a control system which uses the control method, for a longitudinal motion-sensing two-wheeled vehicle.

In order to achieve the above objects, the disclosure adopts the following technical solutions:

A control method for a longitudinal motion-sensing two-wheeled vehicle, includes:

collecting posture data of a human body leaning forward and leaning backward and controlling an output of a circuit drive module by carrying out algorithm operations by means of a central processor to thereby control a rotational output of a motor;

a motor rotor of the motor outputting a movement vector and an acceleration to control a rotation of wheels under the control of the output of the circuit drive module, a motor stator receiving a reaction force during a rotating and outputting process of the motor rotor, and the reaction force being transmitted to a motion-sensing platform through a mechanical structure by the motor stator; and the motion-sensing platform transferring and feeding back the reaction force to a user standing on the motion-sensing platform, thereby adjusting posture data of the motion-sensing platform again by means of a human body posture to achieve a motion-sensing balance control.

Preferably, in the above control method for a longitudinal motion-sensing two-wheeled vehicle, when the human body leans forward, the motion-sensing platform rotates forward, and the motor increases a forward output of the motor rotor, and a vehicle body accelerates forward, and at the same time, the reaction force of the motor stator causes the platform to be lifted in a backward tendency to maintain a certain relative balance state; and when the human body leans backward, the motion-sensing platform rotates backward, and the motor increases a reverse output of the motor rotor, and the vehicle body decelerates forward, and at the same time, the reaction force of the motor stator causes the platform to be lifted in a forward tendency to maintain a certain relative balance state.

A control system for a longitudinal motion-sensing two-wheeled vehicle includes:

a motion-sensing module including a motion-sensing platform and a state posture sensor mounted in the motion-sensing platform;

a central processor connected to state posture sensor data signals; and a circuit drive module disposed between the central processor and a motor, wherein the motor includes a motor rotor and a motor stator, and the motor rotor is transmittingly connected to wheels to drive the wheels to rotate, and the motor stator is mechanically transmittingly connected to the motion-sensing platform.

Compared with the prior art, the beneficial effects of the disclosure are mainly embodied in the following: through the technical solution, the user only needs to adjust the human body posture to achieve the purpose of controlling the balance. The user controls the output of the motor by means of the central processor simply by adjusting the human body posture, thereby controlling the forward movement, backward movement, acceleration, deceleration or stop of the wheels of the two-wheeled vehicle. In addition, at the same time, when the motor is working externally, there is an interaction force between the motor rotor and the motor stator. The reaction force received by the motor stator may be further transferred in real time to the motion-sensing platform equipped with a rotating shaft by means of mechanical transmission to form a negative feedback, so that posture data of the motion-sensing platform is adjusted again by means of the human body posture, thereby achieving a motion-sensing balance control.

BRIEF DESCRIPTION OF THE DRAWINGS

FIG. 1 is a schematic block diagram of structural principles of the disclosure.

DESCRIPTION OF THE EMBODIMENTS

The disclosure will be further described below together with the accompanying drawing and the embodiment.

As shown in FIG. 1, a control method for a longitudinal motion-sensing two-wheeled vehicle includes:

collecting posture data of a human body leaning forward and leaning backward and controlling an output of a circuit drive module by carrying out algorithm operations by means of a central processor to thereby control a rotational output of a motor;

a motor rotor of the motor outputting a movement vector and an acceleration to control a rotation of wheels under the control of the output of the circuit drive module, a motor stator receiving a reaction force during a rotating and outputting process of the motor rotor, and the reaction force being transmitted to a motion-sensing platform through a mechanical structure by the motor stator; and the motion-sensing platform transferring and feeding back the reaction force to a user standing on the motion-sensing platform, thereby adjusting posture data of the motion-sensing platform again by means of a human body posture to achieve a motion-sensing balance control.

When the human body leans forward, the motion-sensing platform rotates forward, and the motor increases a forward output of the motor rotor, and a vehicle body accelerates forward, and at the same time, the reaction force of the motor stator causes the platform to be lifted in a backward tendency to maintain a certain relative balance state; when the human body leans backward, the motion-sensing platform rotates backward, and the motor increases a reverse output of the motor rotor, and the vehicle body decelerates forward, and at the same time, the reaction force of the motor stator causes the platform to be lifted in a forward tendency to maintain a certain relative balance state.

A control system for a longitudinal motion-sensing two-wheeled vehicle includes:

a motion-sensing module including a motion-sensing platform and a state posture sensor mounted in the motion-sensing platform;

a central processor connected to state posture sensor data signals; and a circuit drive module disposed between the central processor and a motor, wherein the motor includes a motor rotor and a motor stator, and the motor rotor is transmittingly connected to wheels to drive the wheels to rotate, and the motor stator is mechanically transmittingly connected to the motion-sensing platform.

Through the technical solution, the user only needs to adjust the human body posture to achieve the purpose of controlling the balance. The user controls the output of the motor by means of the central processor by adjusting the human body posture, thereby controlling the forward movement, backward movement, acceleration, deceleration or stop of the wheels of the two-wheeled vehicle. In addition, at the same time, when the motor is working externally, there is an interaction force between the motor rotor and the motor stator. The reaction force received by the motor stator may be further transferred in real time to the motion-sensing platform equipped with a rotating shaft by means of mechanical transmission to form a negative feedback, so that posture data of the motion-sensing platform is adjusted again by means of the human body posture, thereby achieving a motion-sensing balance control.

Various other corresponding changes and modifications may be made by persons skilled in the art in light of the above-described technical solutions and ideas, and all such changes and modifications are intended to fall within the scope of the claims of the disclosure.

What is claimed is:

1. A control method for a longitudinal motion-sensing two-wheeled vehicle, comprising:

collecting posture data of a human body leaning forward and leaning backward and controlling an output of a circuit drive module by carrying out algorithm operations by means of a central processor to thereby control a rotational output of a motor;

a motor rotor of the motor outputting an acceleration to control a rotation of wheels under the control of the output of the circuit drive module, a motor stator receiving a reaction force during a rotating and outputting process of the motor rotor, and the reaction force being transmitted to a motion-sensing platform through a mechanical structure by the motor stator; and the motion-sensing platform transferring and feeding back the reaction force to a user standing on the motion-sensing platform, thereby adjusting posture data of the motion-sensing platform again by means of a human body posture to achieve a motion-sensing balance control.

2. The control method for a longitudinal motion-sensing two-wheeled vehicle according to claim 1, wherein when the human body leans forward, the motion-sensing platform rotates forward, and the motor increases a forward output of the motor rotor, and a vehicle body accelerates forward, and at the same time, the reaction force of the motor stator causes the platform to be lifted in a backward tendency to maintain a certain relative balance state; and when the human body leans backward, the motion-sensing platform rotates backward, and the motor increases a reverse output of the motor rotor, and the vehicle body decelerates forward, and at the same time, the reaction force of the motor stator causes the platform to be lifted in a forward tendency to maintain a certain relative balance state.

3. A control system for a longitudinal motion-sensing two-wheeled vehicle, which uses the control method according to claim 1, comprising:

a motion-sensing module comprising a motion-sensing platform and a state posture sensor mounted in the motion-sensing platform;

a central processor connected to state posture sensor data signals; and a circuit drive module disposed between the central processor and a motor, wherein the motor comprises a motor rotor and a motor stator, and the motor rotor is transmittingly connected to wheels to drive the wheels to rotate, and the motor stator is mechanically transmittingly connected to the motion-sensing platform.

4. A control system for a longitudinal motion-sensing two-wheeled vehicle, which uses the control method according to claim 2, comprising:

a motion-sensing module comprising a motion-sensing platform and a state posture sensor mounted in the motion-sensing platform;

a central processor connected to state posture sensor data signals; and a circuit drive module disposed between the central processor and a motor, wherein the motor comprises a motor rotor and a motor stator, and the motor rotor is transmittingly connected to wheels to drive the wheels to rotate, and the motor stator is mechanically transmittingly connected to the motion-sensing platform.

* * * * *